(12) United States Patent
Tate et al.

(10) Patent No.: US 12,702,335 B2
(45) Date of Patent: Aug. 11, 2026

(54) UNDERWATER EYE TRACKING SYSTEM AND METHOD

(71) Applicant: FLORIDA INSTITUTE FOR HUMAN AND MACHINE COGNITION INC., Pensacola, FL (US)

(72) Inventors: Connor Tate, Pensacola, FL (US); Savannah Richardson, Pensacola, FL (US); Jeffrey Phillips, Pensacola, FL (US); Timothy Hutcheson, Pensacola, FL (US); Kody Coleman, Pensacola, FL (US)

(73) Assignee: FLORIDA INSTITUTE FOR HUMAN AND MACHINE COGNITION INC., Pensacola, FL (US)

( * ) Notice: Subject to any disclaimer, the term of this patent is extended or adjusted under 35 U.S.C. 154(b) by 0 days.

(21) Appl. No.: 18/804,495

(22) Filed: Aug. 14, 2024

(65) Prior Publication Data

US 2025/0275699 A1 Sep. 4, 2025

Related U.S. Application Data

(60) Provisional application No. 63/548,560, filed on Feb. 1, 2024, provisional application No. 63/532,492, filed on Aug. 14, 2023.

(51) Int. Cl.

| | |
|---|---|
| ***A61B 5/16*** | (2006.01) |
| ***A61B 3/113*** | (2006.01) |
| ***A61B 3/14*** | (2006.01) |
| ***A61B 5/00*** | (2006.01) |
| ***B63C 11/26*** | (2006.01) |
| *B63C 11/12* | (2006.01) |

(52) U.S. Cl.

CPC .............. *A61B 5/163* (2017.08); *A61B 3/113* (2013.01); *A61B 3/14* (2013.01); *A61B 5/6803* (2013.01); *B63C 11/26* (2013.01); *B63C 11/12* (2013.01)

(58) Field of Classification Search

CPC ......... A61B 5/6803; A61B 5/486; A61B 5/16; A61B 5/163; A61B 2090/502; G06F 3/013

See application file for complete search history.

(56) References Cited

U.S. PATENT DOCUMENTS

| | | | | |
|---|---|---|---|---|
| 2007/0273611 A1* | 11/2007 | Torch | ..................... | A61B 3/112 345/8 |
| 2018/0246568 A1* | 8/2018 | Holz | ..................... | G06V 40/20 |
| 2024/0000509 A1* | 1/2024 | Xiao | ..................... | A61B 90/39 |

* cited by examiner

*Primary Examiner* — Gerald Johnson

(74) *Attorney, Agent, or Firm* — Jacob M. Ward; Ward Law Office LLC

(57) ABSTRACT

A system and method wherein a face mounted eye-tracking system is mounted in a dive mask. The mask mounted occulometric system has a novel configuration and enclosure to provide in situ occulometrics and neurological assessment.

20 Claims, 7 Drawing Sheets

50
52
54
40
46
38
42
44
48

56
42
58
60
62
48
46

UNDERWATER EYE TRACKING SYSTEM AND METHOD

CROSS-REFERENCES TO RELATED APPLICATIONS

This non-provisional patent application claims the benefit, pursuant to 37 C.F.R. section 1.53(c), of two previously filed provisional patent applications. The parent applications are: U.S. App. No. 63/532,492 filed on Aug. 14, 2023, and U.S. App. No. 63/548,560 filed on Feb. 1, 2024. Both provisional applications listed the same inventors as the present application.

STATEMENT REGARDING FEDERALLY SPONSORED RESEARCH OR DEVELOPMENT

Work on this project has been funded by the United States Government, Office of Naval Research, pursuant to Grantor No. N00014-20-1-2340.

MICROFICHE APPENDIX

Not Applicable

BACKGROUND OF THE INVENTION

1. Field of the Invention

The present invention pertains to the field of human physiology monitoring. More specifically, the invention comprises a face mounted eye-tracking system that can provide in situ occulometrics and neurological assessment.

2. Description of the Related Art

The present invention provides the ability to monitor and assess a diver without unduly interfering with the diver's work. Divers are exposed to a range of environmental stressors that can negatively affect health status and outcomes. Environmental threats include nitrogen narcosis, oxygen toxicity, hypercapnia, and hypoxia. Such threats often arise from malfunctioning life-support equipment. Divers are trained to recognize the onset of many of these conditions, but the conditions themselves tend to impair cognitive functioning and self-recognition is therefore always risky (even for those conditions where self-recognition is possible).

Automated underwater operator health status monitoring is therefore an essential component of any mitigation strategy. Negative changes in health status must be identified as early as possible to extend the viable mitigation window prior to injury or incapacitation. The present invention provides a system and method for identifying these negative changes.

BRIEF SUMMARY OF THE INVENTION

The inventors have developed a face mounted eye-tracking system for use with a prior art dive mask-such as an INTERSPIRO DIVATOR MK11 dive mask. The mask-mounted occulometric system has a novel configuration and enclosure to provide in situ occulometrics and neurological assessment. Embedded LEDs provide spot checks of neurological status based on the pupil's response to light, focal stability, blink rate, and saccadic velocity. The system also possesses the ability to detect off-nominal eye states (such as closed eyes, irregular pupil location, or eye movements). The system is adjustable, adapted to the diver and removable via the mask visor.

REFERENCE NUMERALS USED IN THE DRAWING VIEWS

Figure 1:
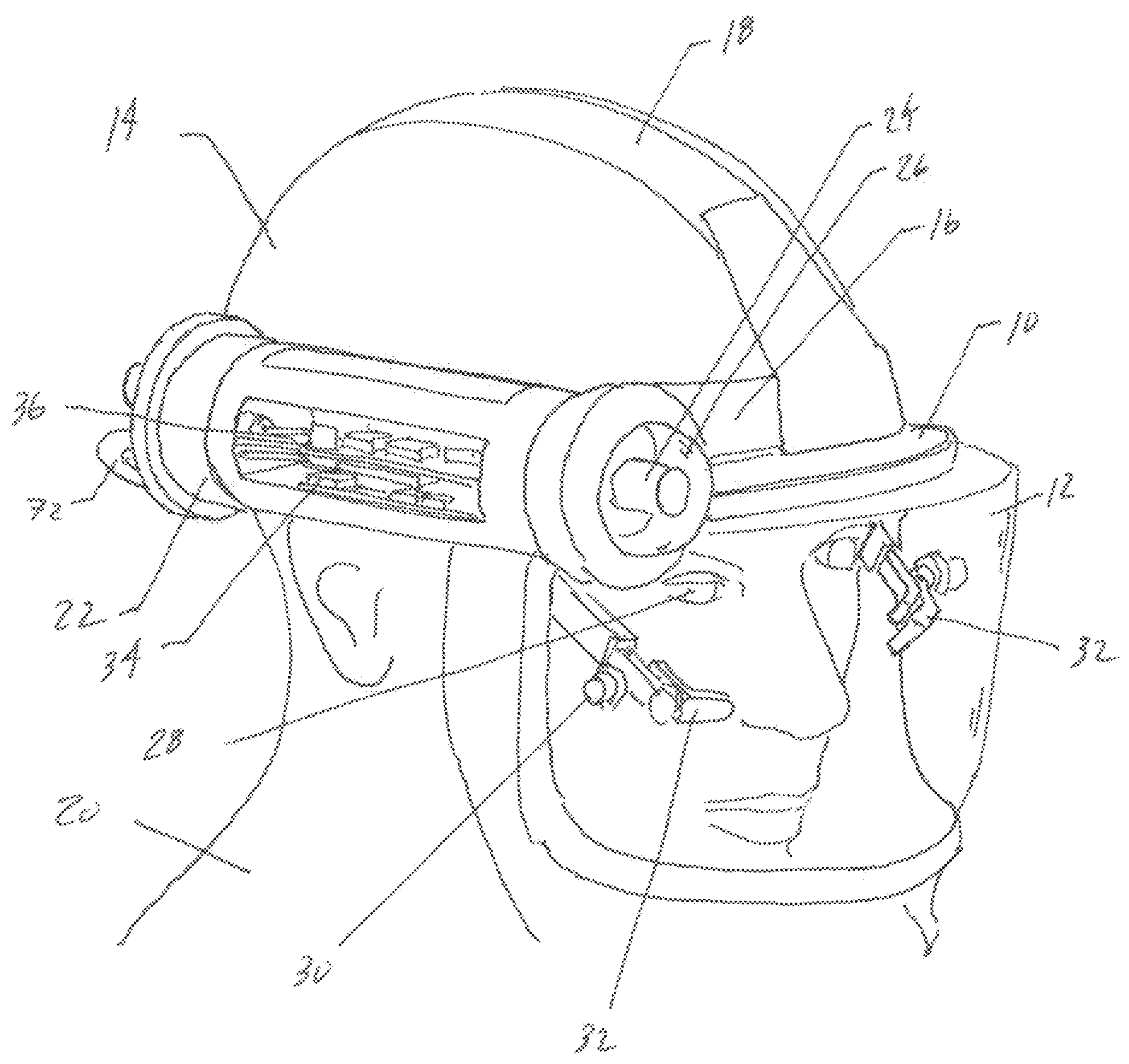
FIG. 1 is a perspective view, showing a dive mask incorporating the invention.

10 dive mask
12 mask window
14 diver
16 band
18 superior strap
20 diver
22 electronics enclosure
24 world view camera
26 lens
28 eye
30 mount
32 camera
34 computer
36 hub
38 integrated tracking system
40 inner cover
42 outer cover
44 ball mount
46 cable
48 waterproof via
50 LED lens
52 IR lens
54 camera lens
56 LED
58 IR emitter
60 camera
62 flex circuit
64 pupil
66 first end cap
68 second end cap
70 waterproof via
72 cable
74 conductors
76 laptop
78 interface
80 water level

DETAILED DESCRIPTION OF THE INVENTION

The inventive device can be adapted for use in a wide variety of environments. This disclosure pertains to an embodiment configured for use in dive masks. FIG. 1 shows a version configured for use with the INTERSPIRO MKII dive mask, as marketed by Interspiro of Stockholm, Sweden. The inventive eye tracking device is integrated into the dive mask for use in submerged underwater field operations.

Dive mask 10 incorporates a large mask window 12. The mask window itself provides one or more mounts 30. These are often clamping devices placed through a bore in the window material. Band 16 passes around the head of diver 20. Superior strap 18 passes over the top of the head and attaches to the posterior portion of the band.

Electronics enclosure 22 is attached to the mask assembly. It may be mounted on the side of the band and/or attached to the frame of the mask window. World view camera 24 is contained within the electronics enclosure in this example. The world view camera is directed forward through lens 26. The world view camera preferably provides a wide field-of-view, so that a remote observer can see the environment directly in front of the diver's face. One or more forward-facing lights can be provided as well.

FIG. 1 includes a cutaway so the reader can visualize the interior of electronics enclosure 22. Monitoring and communication electronics are contained within enclosure 22. In the example shown, computer 34 and hub 36 are present. The computer performs local processing by retrieving and executing locally-stored software. Hub 36 facilitates communication with the eye tracking devices, the world view camera, external monitors, etc. Cables 72 pass into and out of the enclosure 22 through waterproof vias. The interior of enclosure 22 may be flooded with a suitable liquid to maintain neutral buoyancy (Air in the enclosure would tend to lift the mask assembly upward). Dielectric silicone liquid may be used to flood the interior.

Figures 2, 3:
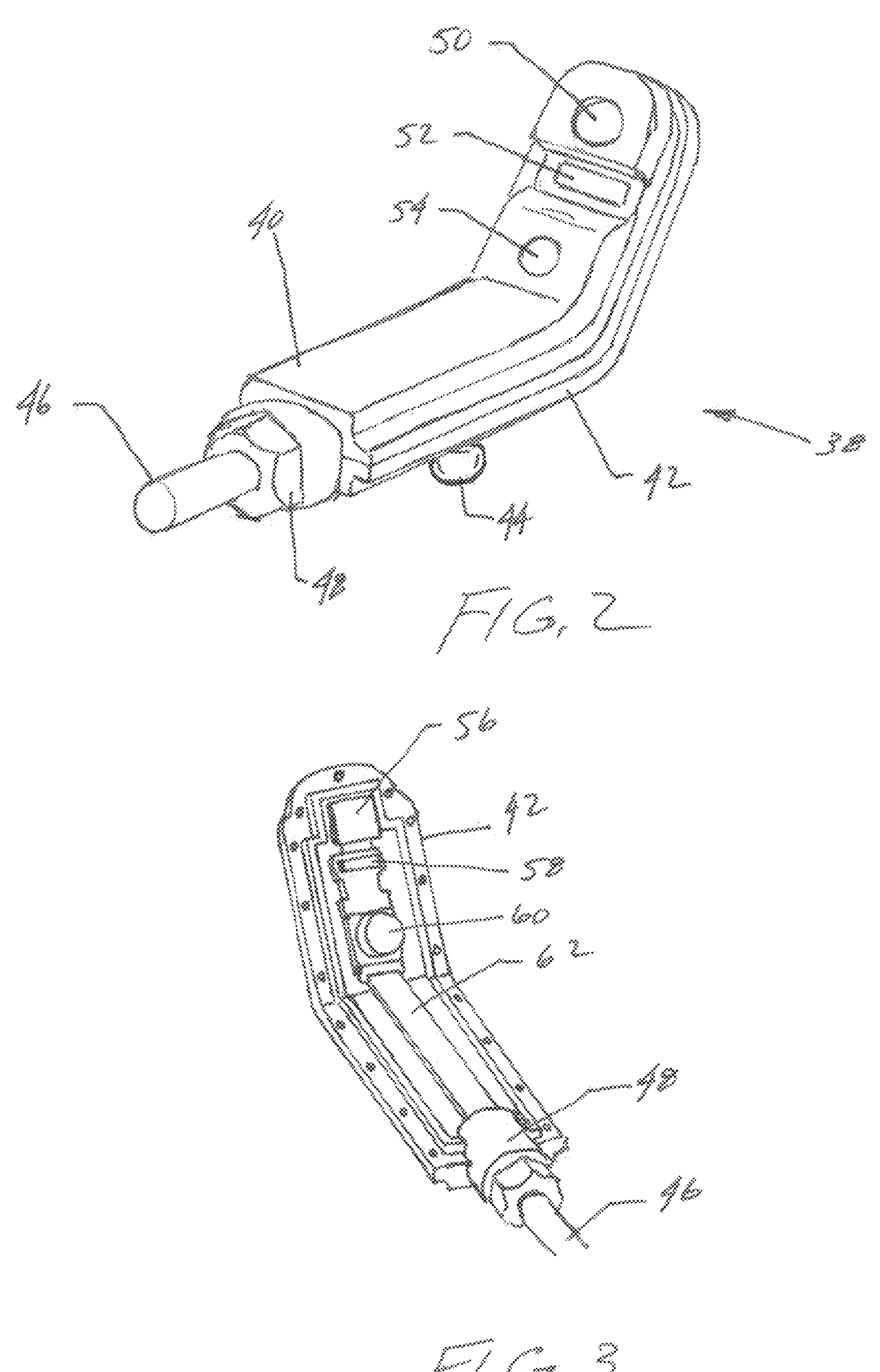
FIG. 2 is a perspective view, showing an integrated tracking system according to the present invention.
FIG. 3 is a perspective view, showing the tracking system of FIG. 2 with the inner cover removed to show internal details.

It is preferable to provide a compact and integrated package for the emitters and sensors used in the inventive system. FIGS. 2 and 3 illustrate such a package. FIG. 2 shows integrated tracking system 38. Inner cover 40 and outer cover 42 are sealed together to encapsulate a set of enclosed components-typically a conventional LED, an infrared emitter, and a camera. The LED transmits light through LED lens 50. The IR emitter transmits through IR lens 52. The camera—which is typically an IR capable camera—views through camera lens 54. Cable 46 contains multiple electrically insulated conductors. These pass into the interior of integrated tracking system 38 through waterproof via 48.

FIG. 3 shows the assembly with inner cover 40 removed. The reader will note how LED 56, IR emitter 58, and camera 60 are mounted within the sealed interior. These components are electrically connected to cable 46 in this example by flex circuit 62. A sealing perimeter is provided to waterproof the assembly. Fasteners can be used to join inner cover 40 and outer cover 42. They may also be glued or otherwise fused together.

Waterproofing gaskets can be added to increase the pressure resistance. The internal components can optionally be potted into a water-resistant material.

Figure 4:
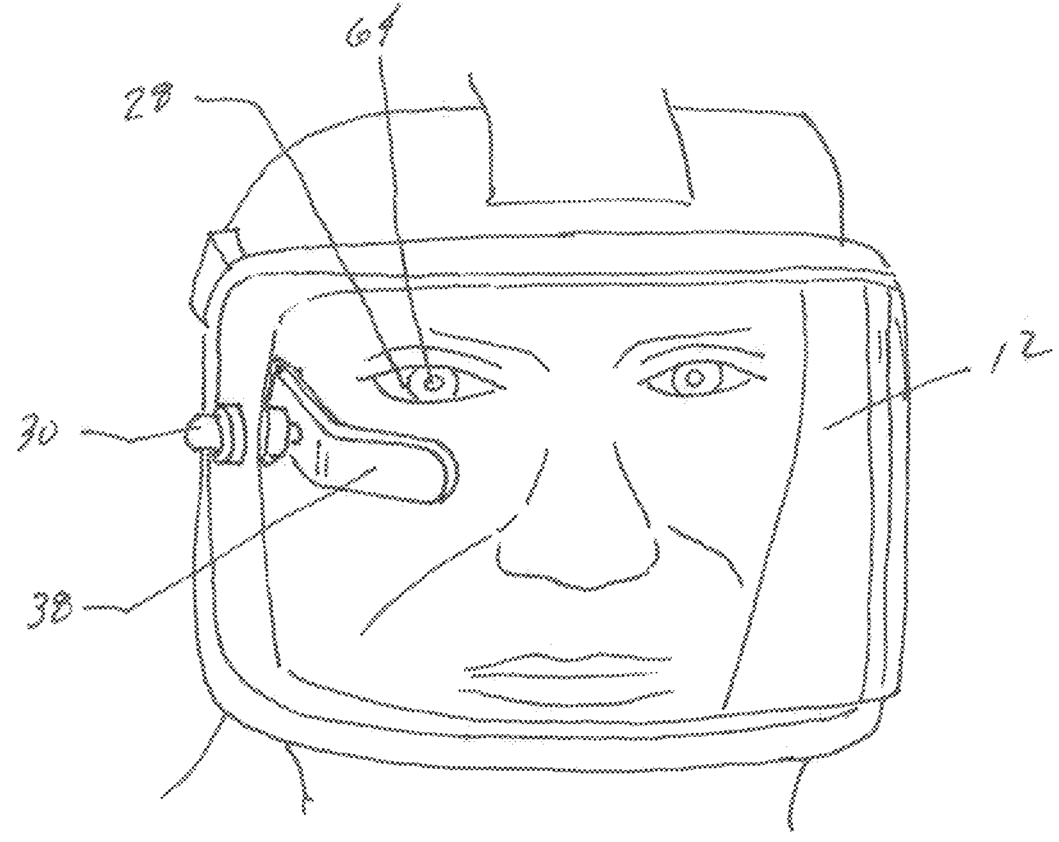
FIG. 4 is a perspective view, showing a mask incorporating the integrated tracking system as shown in FIG. 2.

FIG. 4 shows an exemplary mounting of integrated tracking system 38 inside mask window 12 of a diving mask. Mount 30 is preferably made adjustable to account for variations in facial anatomy. The tracking system 38 is positioned so that LED 56, IR emitter 58, and camera 60 are directed toward pupil 64 of eye 28.

Figure 5:
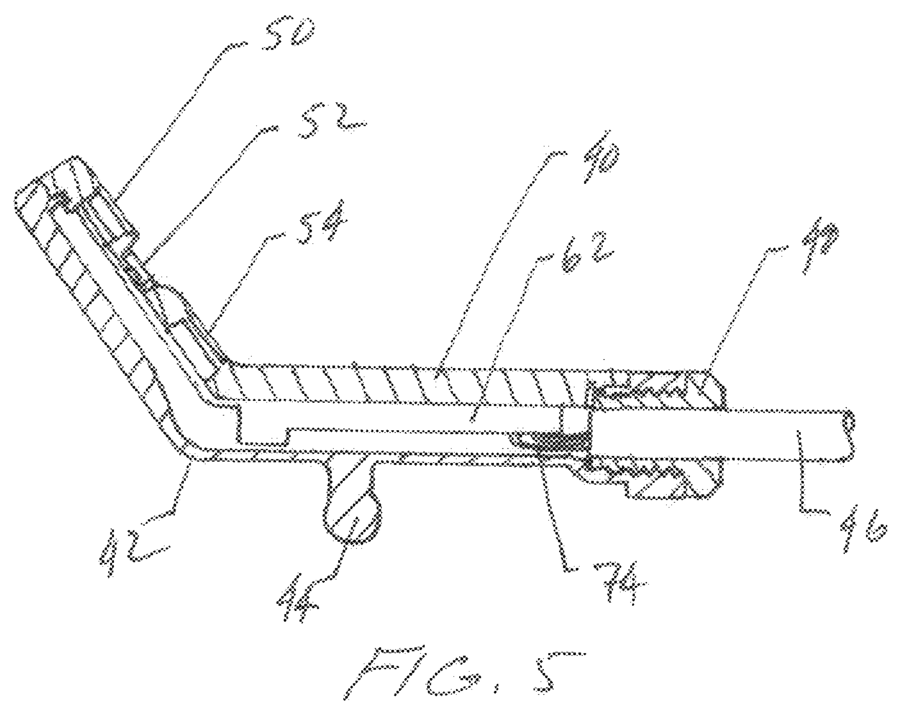
FIG. 5 is a sectional elevation view, showing internal details of the integrated tracking system.
Figure 6:
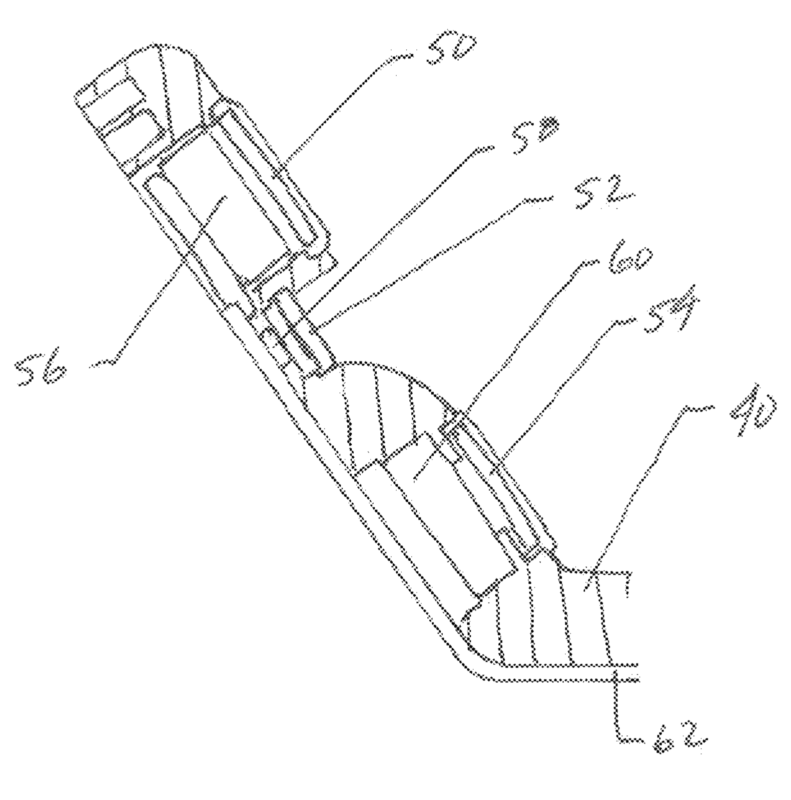
FIG. 6 is a detailed sectional elevation view, showing more internal details of the integrated tracking system.

FIGS. 5 and 6 show sectional views through the exemplary integrated tracking system 38. FIG. 5 shows how inner cover 40 and outer cover 42 clamp together to house the internal components. Conductors 74 emerge from cable 46 and connect to flex circuit 62. The flex circuit carries the signals to and from the internal components—the LED, the IR emitter, and the camera in this example. Waterproof via 48 seals the entrance of the cable.

Ball mount 44 extends laterally from outer cover 44. This ball mount can be clamped into an adjustable ball-and-socket mount that is attached to the mask window or some other mounting point on the mask assembly. The ball mount allows the integrated tracking system to be pivoted as desired and then locked into position.

FIG. 6 is a detailed view in the vicinity of LED 56, IR emitter 58, and camera 60. In this example, inner cover 40 includes recesses that capture LED lens 50 over the top of LED 56, IR lens 52 over the top of IR emitter 58, and camera lens 54 over the top of camera 60. These provide a waterproof seal for the operating depth range of the device.

Figure 7:
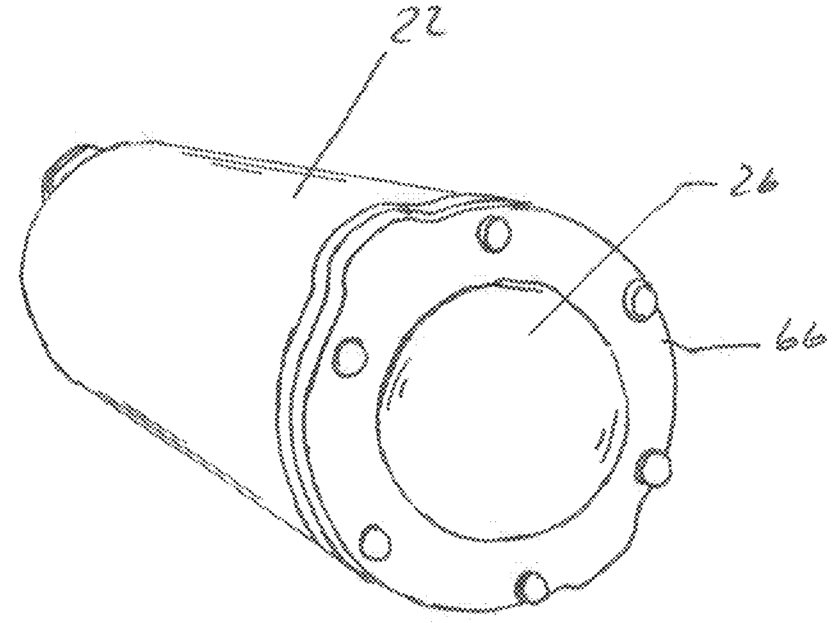
FIG. 7 is a perspective view, showing a first end of the electronics enclosure.
Figure 8:
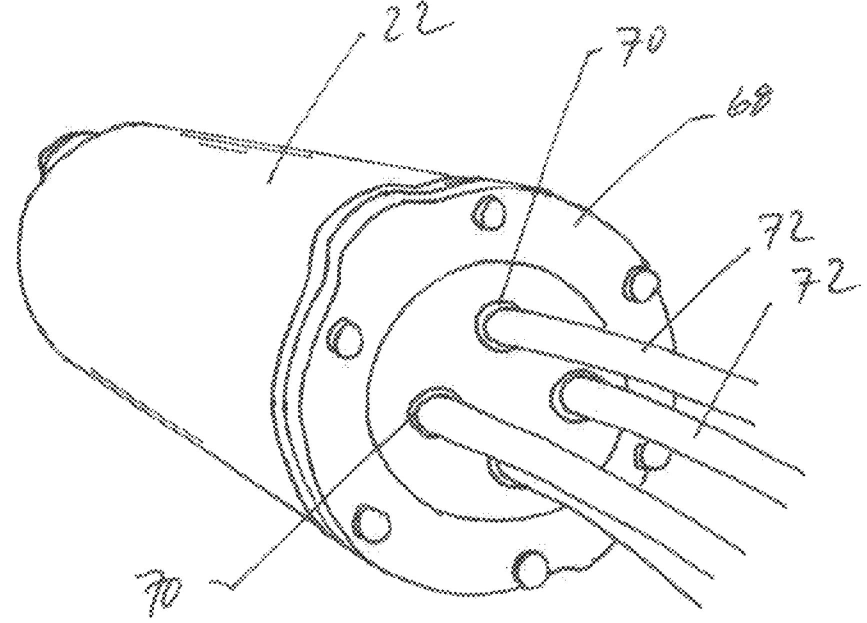
FIG. 8 is a perspective view, showing a second end of the electronics enclosure.

FIGS. 7 and 8 show additional details of electronics enclosure 22. First end cap 66 mounts lens 26. This assembly is connected to the first end of the cylindrical electronics enclosure 22. FIG. 8 shows second end cap 68, which is attached to the second end of electronics enclosure 22. Multiple waterproof vias 70 are provided so that electrical cables 72 can pass through second end cap 68. Cables 72 connect the electronics inside the electronics enclosure 22 to one or more instances of integrated tracking system 38. They also typically connect the electronics to an external monitoring station (often on a surface vessel or platform).

The invention can be realized using a wide variety of hardware and software. An above-water laptop is typically used to acquire and process diver eye tracking data. This laptop runs PUPIL CORE open-source software (as marketed by Pupil Labs of Berlin, Germany) to acquire diver eye tracking data.

In the example shown in FIG. 1, computer 34 is a single board computer known as a RASPBERRY PI ZERO, marketed by Raspberry Pi, Ltd., of England. Hub 36 is a ZERO 4U four-port USB 3.0 hub as marketed by Adafruit Industries of New York, NY. This hub is used to integrate the various camera feeds and communicate to the laptop and the PUPIL CORE software. The hub is compatible with the RASPBERRY PI ZERO version 1.3. Other hubs may be substituted in other embodiments.

Camera 60 in the exemplary embodiment of FIG. 3 is a Model No. WS-NK001 S2.0infrared mini USB camera made in Guangdong, China. It features dual lenses. The IR capable camera is used for eye tracking. The world view camera is a 1080p wide angle camera. This is a low light camera for use in marine robotics. It is marketed by BLUEROBOTICS of Torrance, California.

Dotstar and Neopixel are micro LEDs that can be used to elicit pupil latency measures. The LEDs are preferably controlled by the RASPBERRY PI ZERO computer. The LEDs can generate alternating flash patterns that are useful in detecting pupil latency and measuring saccadic velocity (speed of movement during rapid involuntary eye movements).

The exemplary waterproof electronics enclosure shown in FIG. 1 is 50 mm×150 mm (2 inches×5.9 inches). It is available in either cast acrylic (rated to a depth of 250 m) or aluminum (rated to a depth of 950 m). The housing houses the USB hub for computer and sensor interfacing, the world view camera, and the RASPBERRY PI ZERO computer. The internal void space creates 2.58 Newtons of positive buoyancy, so it is desirable to offset the buoyancy force with added weight. For this reason, the aluminum version is preferred. It is also possible to fil the void with dielectric silicone oil to provide neutral buoyancy.

The acrylic dome mounted to one end of the enclosure is designed to be optically clear and suitable for use with the worldview low light USB camera. The four-port end cap shown in FIG. 8 closes the opposite end of the electronics enclosure. It has machined O-ring interfaces, a locking cord, anti-rotation features, and M10 threaded holes for the waterproof cable penetrators (rated to a depth of 950 m).

The materials used in the development of the mounts and enclosures are all low to no volatile organic compound emissions. This is important for the safety of the diver and the prevention of expansion and decompression stress on the equipment when alternating from submerged to unsubmerged operation. The SLS additive manufacturing process has been chosen for production because of the solid, layerless fabrication.

Optically clear visible and near-infrared light transmission lenses have been embedded in the enclosure to allow for the operation of imaging cameras and LED diodes.

FIG. 4 illustrates the integrated tracking system 38 mounted inside the dive mask and positioned to monitor the right eye 28. In many instances a second integrated tracking system will be mounted on the opposite side of the mask to simultaneously monitor the right eye (A dual installation is shown in FIG. 1).

Figure 9:
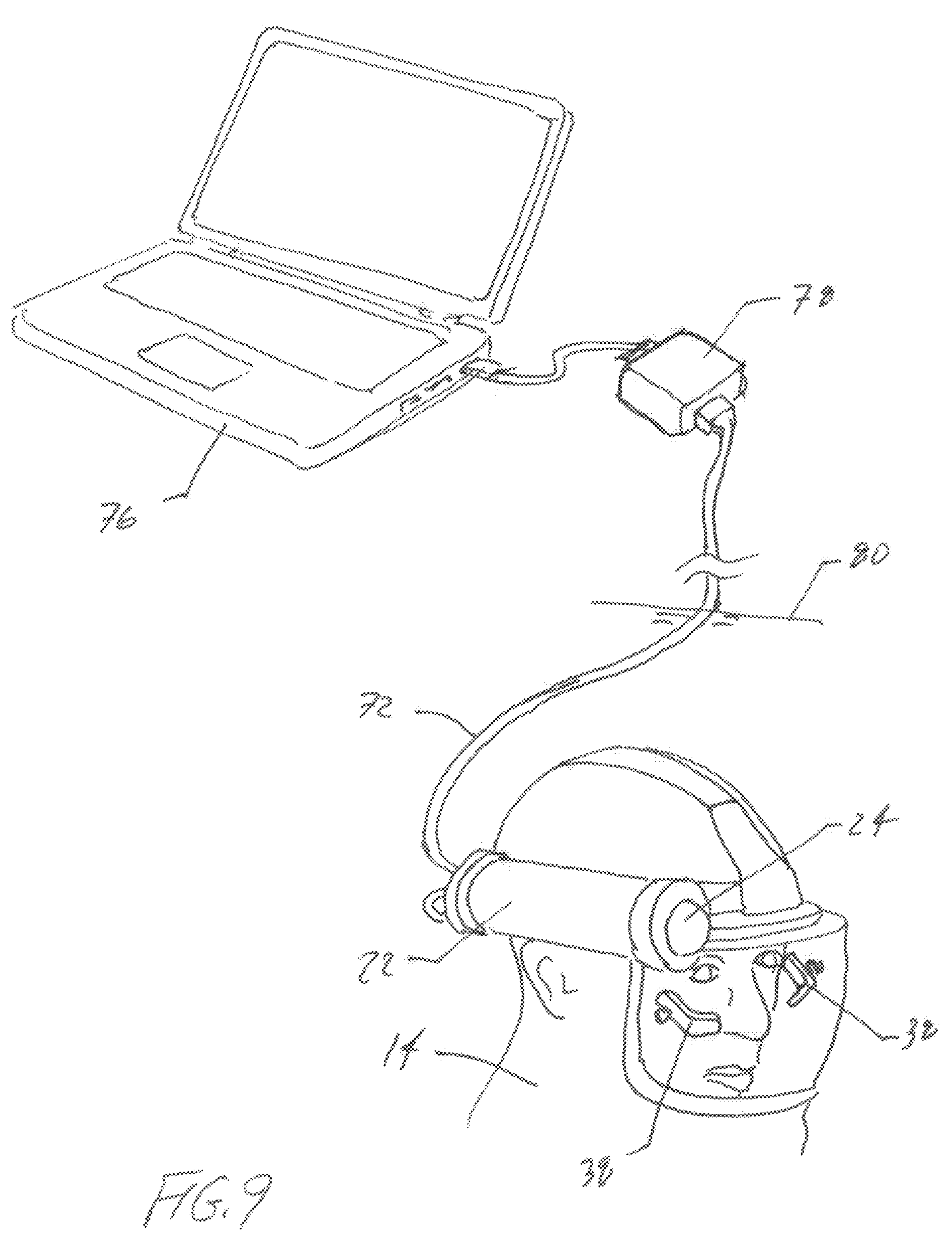
FIG. 9 is a perspective view, showing the connections used for remote monitoring of a diver using the inventive system.

FIG. 9 shows an operative environment in which the invention is used. Laptop 76 is used to monitor the status of diver 14. The laptop is typically maintained on a surface vessel or platform —well above water level 80. The laptop communicates with interface 78. Cable 72 connects interface 78 to the hub within electronics enclosure 22 mounted on the dive mask. The operator of the laptop can typically see the feed from world view camera 24, so the operator can see what is in front of the diver. Cables are used to connect the integrated tracking systems 38 to the hub within the electronics enclosure.

Integrated tracking systems 38 monitor the movements of the diver's eyes. The output of the cameras within the tracking systems can also be displayed to the laptop operator. The cameras 60 (see FIG. 3) are preferably capable of monitoring into the infrared range. IR light can be produced by IR emitters 58 as needed. LED 56 provides visual spectrum light for other actions—such as testing the reaction of the diver's eyes to light stimuli.

The use of the IR emitter and the IR-capable camera allows the diver's eye movements to be tracked without interfering with the diver's vision. A diver often works in a low-light environment and shining visible-spectrum light into the eye is undesirable. The use of IR light for eye tracking is therefore advantageous because eye tracking can proceed without the diver even being aware of it.

The hardware can thus be used to monitor for threats to the diver's health status. As explained previously, divers are exposed to a range of environmental stressors that can negatively affect health status and outcomes. Environmental threats include nitrogen narcosis, oxygen toxicity, hypercapnia, and hypoxia. Such threats often arise from malfunctioning life-support equipment. Underwater operator health status monitoring is an essential component to any viable mitigation strategy. Negative changes in health status must be identified as early as possible to extend the viable mitigation window prior to injury or incapacitation.

The LEDs 56 provide spot checks of neurological status based on the pupil's response to light. The eye tracking camera can be used to measure focal stability, blink rate and saccadic velocity (velocity of involuntary eye movements). The system also possesses the ability to detect off-nominal eye states (i.e., closed eyes, irregular pupil location or unusual eye movements). The system is adjustable, adapted to the diver and removable via the mask visor.

For the installations employing two integrated tracking systems (one for each eye), the LEDs and camera can be used to evaluate pupillary reflexes for both eyes. The LEDs in each integrated tracking system 38 are configured to project light onto the proximal eye but not the distal eye. This allows the system to test for the pupillary light reflex. The system 38 proximate the right eye can project light into the right eye. The system 38 proximate the left eye can then monitor the left eye to see if the left pupil contracts in response to light being applied to the right eye. An abnormal response is useful in monitoring for neurological impairment of the diver.

The preceding descriptions contains significant detail regarding the novel aspects of embodiments of the present invention. It should not be construed, however, as limiting the scope of the invention but rather as providing illustrations of the preferred embodiments of the invention. Thus, the scope of the invention should be fixed by the claims ultimately presented, rather than by the examples given.

Having described our invention, we claim:

1. A method for monitoring the health status of a submerged diver wearing a mask, comprising:

mounting a first integrated tracking system in an interior of the mask, the first integrated tracking system including a visual spectrum light source, an infrared light source, and a camera directed toward a first eye of the diver;

mounting a waterproof electronics enclosure containing a hub on an exterior of the mask;

connecting the first integrated tracking system to the hub via a first cable passing through a waterproof via in the waterproof electronics enclosure;

providing a monitoring computer at a surface location above water level while the diver is submerged underwater;

connecting the hub to the monitoring computer via a tether cable extending from the submerged diver to the surface location;

tracking movements of the first eye using the infrared light source and the camera; and monitoring a health status of the diver at the surface location based on the eye tracking while the diver remains submerged underwater.

2. The method of claim 1, further comprising using the visual spectrum light source to provide a visual stimulus to the first eye and monitoring a response of the first eye to the visual stimulus using the camera.

3. The method of claim 1, wherein the monitoring detects a dive-related condition including a member selected from a group consisting of: nitrogen narcosis, oxygen toxicity, hypercapnia, and hypoxia.

4. The method of claim 1, further comprising:

providing a second integrated tracking system in the interior of the mask, the second integrated tracking system including a second visual spectrum light source, a second infrared light source, and a second camera directed toward a second eye of the diver; and connecting the second integrated tracking system to the hub.

5. The method of claim 4, further comprising simultaneously monitoring movements of both eyes using each of the first and second integrated tracking systems.

6. The method of claim 4, further comprising:

applying a visual stimulus to one eye using one of the first visual spectrum light source of the first integrated tracking system and the second visual spectrum light source of the second integrated tracking system; and monitoring for a consensual pupillary reflex in the other eye using the other of the first integrated tracking system and the second integrated tracking system.

7. An apparatus for monitoring the health status of a submerged diver, comprising:

a dive mask;

a first integrated tracking system mounted within an interior of the dive mask and including a visual spectrum light source, an infrared light source, and a camera directed toward a first eye position;

a waterproof electronics enclosure mounted on an exterior of the dive mask and containing a hub;

a first waterproof cable connecting the first integrated tracking system to the hub through a waterproof via in the waterproof electronics enclosure; and a tether cable extending from the hub for connection to a monitoring computer at a surface location.

8. The apparatus of claim 7, wherein the waterproof electronics enclosure includes a first end cap and a second end cap, the waterproof via disposed in the second end cap.

9. The apparatus of claim 7, further comprising a second integrated tracking system mounted within the interior of the dive mask and directed toward a second eye position, the second integrated tracking system connected to the hub via a second waterproof cable.

10. The apparatus of claim 9, wherein the second integrated tracking system is connected to the hub via a second waterproof cable passing through the waterproof electronics enclosure.

11. The apparatus of claim 9, wherein the waterproof electronics enclosure includes a first end cap and a second end cap, the waterproof via disposed in the second end cap.

12. The apparatus of claim 11, wherein the first end cap includes a lens for a world view camera mounted within the waterproof electronics enclosure.

13. The apparatus of claim 7, further comprising a world view camera mounted within the waterproof electronics enclosure and directed outwardly through the waterproof electronics enclosure.

14. The apparatus of claim 7, wherein the sealed electronics housing contains a computer for local processing of eye tracking data prior to transmission to the surface monitoring station.

15. The apparatus of claim 7, wherein the first integrated tracking system comprises an inner cover and an outer cover sealed together to form a waterproof housing.

16. The apparatus of claim 15, wherein the inner cover includes a first recess that captures an LED lens over the visual spectrum light source, a second recess that captures an IR lens over the infrared light source, and a third recess that captures a camera lens over the camera.

17. The apparatus of claim 7, wherein the first integrated tracking system includes a flex circuit electrically connecting the visual spectrum light source, the infrared light source, and the camera.

18. The apparatus of claim 7, wherein the first integrated tracking system includes a ball mount extending laterally from the first integrated tracking system for adjustable positioning of the first integrated tracking.

19. The apparatus of claim 7, wherein the waterproof electronics enclosure contains dielectric silicone liquid for neutral buoyancy.

20. An apparatus for monitoring the health status of a submerged diver, comprising:

a dive mask;

a first integrated tracking system mounted within an interior of the dive mask and including a visual spectrum light source, an infrared light source, and a camera directed toward a first eye position, wherein the first integrated tracking system includes an inner cover and an outer cover sealed together to form a waterproof housing, wherein the inner cover includes a first recess that captures an LED lens over the visual spectrum light source, a second recess that captures an IR lens over the infrared light source, and a third recess that captures a camera lens over the camera, wherein the first integrated tracking system includes a flex circuit electrically connecting the visual spectrum light source, infrared light source, and camera, and wherein the first integrated tracking system includes a ball mount extending laterally from the system for adjustable positioning;

a second integrated tracking system mounted within the interior of the dive mask and directed toward a second eye position;

a waterproof electronics enclosure mounted on an exterior of the dive mask and containing a hub, wherein the waterproof electronics enclosure includes a first end cap and a second end cap, wherein the first end cap includes a lens for a world view camera mounted within the waterproof electronics enclosure, and wherein the waterproof electronics enclosure contains a computer for local processing of eye tracking data and dielectric silicone liquid for neutral buoyancy;

a world view camera mounted within the waterproof electronics enclosure and directed outwardly through the waterproof electronics enclosure;

a first waterproof cable connecting the first integrated tracking system to the hub through a waterproof via disposed in the second end cap of the waterproof electronics enclosure;

a second waterproof cable connecting the second integrated tracking system to the hub and passing through the waterproof electronics enclosure; and a tether cable extending from the hub for connection to a monitoring computer at a surface location.

* * * * *